(12) United States Patent
Mouchawar et al.

(10) Patent No.: US 6,345,198 B1
(45) Date of Patent: Feb. 5, 2002

(54) IMPLANTABLE STIMULATION SYSTEM FOR PROVIDING DUAL BIPOLAR SENSING USING AN ELECTRODE POSITIONED IN PROXIMITY TO THE TRICUSPID VALVE AND PROGRAMMABLE POLARITY

(75) Inventors: Gabriel Mouchawar, Newhall; James D. Causey, III, Simi Valley; Kenneth Valikai, Palos Verdes Pen., all of CA (US)

(73) Assignee: Pacesetter, Inc., Sylmar, CA (US)

( * ) Notice: Subject to any disclaimer, the term of this patent is extended or adjusted under 35 U.S.C. 154(b) by 0 days.

(21) Appl. No.: 09/364,537

(22) Filed: Jul. 29, 1999

Related U.S. Application Data

(63) Continuation-in-part of application No. 09/012,856, filed on Jan. 23, 1998, now Pat. No. 5,948,014.

(51) Int. Cl.$^7$ ................................................. A61N 1/05
(52) U.S. Cl. ........................ 607/4; 607/123; 600/374
(58) Field of Search .......................... 607/123, 122, 607/4, 5, 9, 17; 600/374

(56) References Cited

U.S. PATENT DOCUMENTS

| | | | |
|---|---|---|---|
| 3,825,015 A | 7/1974 | Berkovits | 128/404 |
| 3,903,897 A | 9/1975 | Woollons et al. | 128/419 |
| 4,154,247 A | 5/1979 | O'Neill | 128/419 |
| 4,481,953 A | * 11/1984 | Gold et al. | 128/786 |
| 4,585,004 A | 4/1986 | Brownlee | 128/419 |
| 4,624,265 A | 11/1986 | Grassi | 128/784 |
| 4,664,120 A | 5/1987 | Hess | 128/642 |
| 4,711,027 A | 12/1987 | Harris | 29/869 |
| 4,962,767 A | 10/1990 | Brownlee | 128/786 |
| 5,172,694 A | 12/1992 | Flammang et al. | 128/642 |
| 5,304,219 A | 4/1994 | Chernoff et al. | 607/122 |
| 5,522,855 A | 6/1996 | Hoegnelid | 607/9 |
| 5,534,022 A | * 7/1996 | Hoffmann et al. | 607/122 |
| 5,948,014 A | * 9/1999 | Valikai | 607/123 |
| 6,055,457 A | * 4/2000 | Bonner | 607/123 |
| 6,119,043 A | * 9/2000 | Hsu et al. | 607/123 |
| 6,157,862 A | * 12/2000 | Brownlee et al. | 607/123 |

\* cited by examiner

*Primary Examiner*—Kennedy Schaetzle

(57) ABSTRACT

A single-pass pacing and/or shocking lead system is capable of sensing cardiac signal in the atrium and the ventricle in a "bipolar fashion" using a three-electrode structure: a first electrode in the atruim, a second electrode in the ventricle just below the tricuspid valve, and a third in the ventricle.

2 Claims, 4 Drawing Sheets

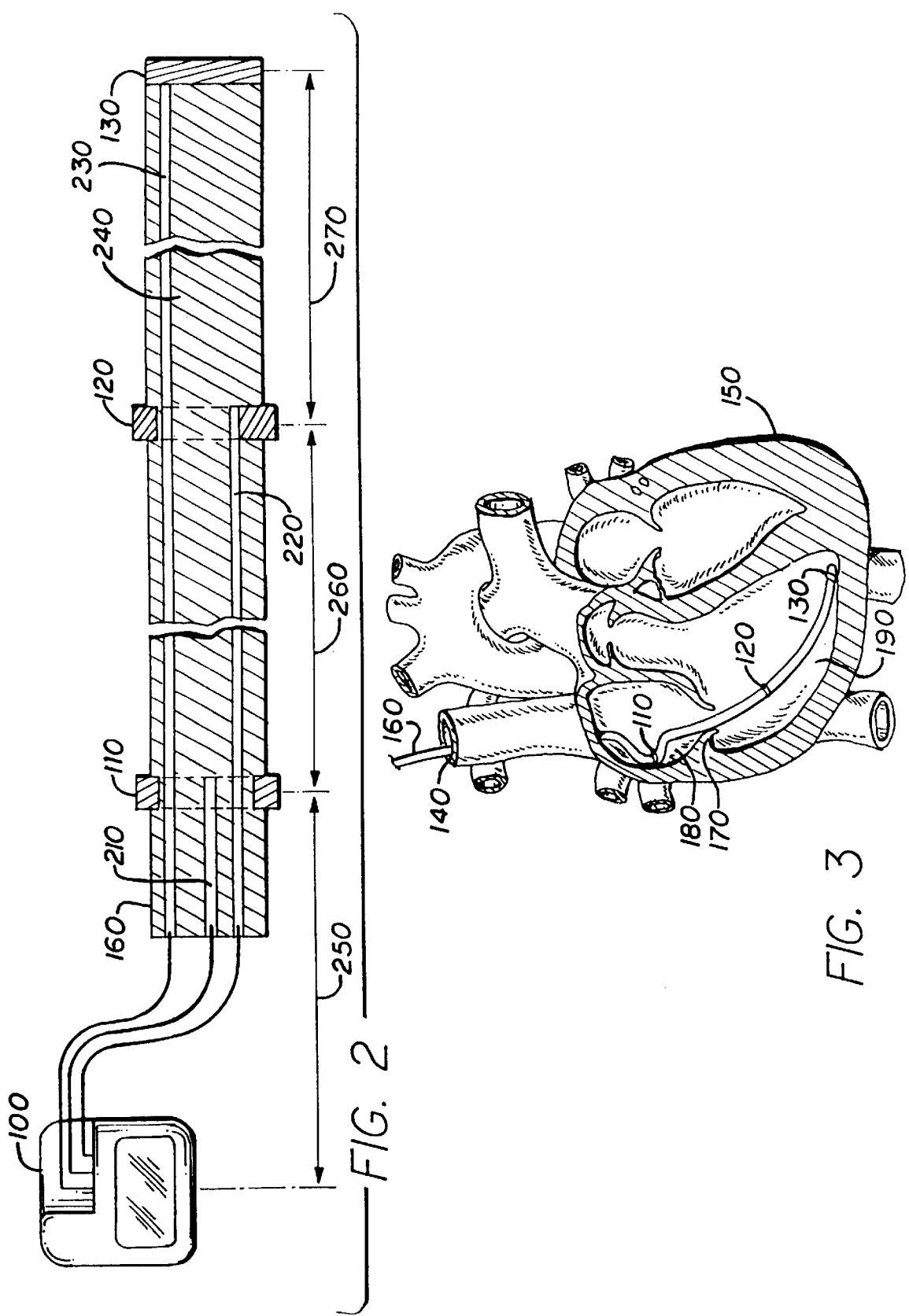

IMPLANTABLE STIMULATION SYSTEM FOR PROVIDING DUAL BIPOLAR SENSING USING AN ELECTRODE POSITIONED IN PROXIMITY TO THE TRICUSPID VALVE AND PROGRAMMABLE POLARITY

CROSS-REFERENCE TO RELATED APPLICATIONS

This application is a continuation-in-part of application Ser. No. 09/012,856, filed Jan. 23, 1998, now U.S. Pat. No. 5,948,014.

FIELD OF THE INVENTION

The invention generally relates to implantable stimulation devices such as cardiac stimulation devices, cardioverters and defibrillators. More particularly, this invention relates to an implantable stimulation system having a single-pass lead which delivers stimulation therapy and is capable of a plurality of programmable sensing polarities, including bipolar atrial and ventricular sensing with respect to an electrode positioned near the tricuspid valve.

BACKGROUND OF THE INVENTION

Implantable stimulation devices, such as cardiac stimulation devices and implantable cardioverter-defibrillators (hereinafter referred to as ICDs), are often used to remedy improper heart function. These devices generally provide an electrical pulse to a selected area of the heart that is not (in terms of timing or strength) adequately receiving its natural pulse. Under abnormal cardiac conditions, and particularly cardiac rhythm disturbances, stimulation therapy is applied to remedy several forms of cardiac arrhythmias (rhythm disturbances) including bradycardias, AV conduction block, supraventricular tachycardias, and atrial and ventricular ectopic arrhythmias.

There are essentially two kinds of stimulation devices: single-chamber and dual-chamber. Single-chamber stimulation devices are capable of sensing and pacing in only one of the atrium or the ventricle. Dual-chamber stimulation devices are capable of sensing and pacing in both the atrium and the ventricle. There are many modes of dual-chamber pacing such as VDD (paces in the ventricle only, senses in the atrium and ventricle), DVI (paces in the atrium and ventricle, and senses in the ventricle only), DDI (senses and paces in both the atrium and ventricle), and DDD (senses and paces in both the atrium and ventricle, with an inhibited and triggered response to sensing).

A letter "R" is sometimes added to these stimulation device modes to indicate the stimulation device's ability to provide rate-modulated (also sometimes called rate-responsive or rate-adaptive) pacing in response to input from an independent sensor. For instance, a DDDR stimulation device is capable of adapting to the need to increase a patient's heart rate in response to physiologic stress in the absence of intrinsic response from a patient's sinus node.

Dual-chamber ICDs are also known in the art to proved pacing, cardioversion and defibrillation therapy in both chambers of the heart.

A stimulation device uses a lead system to perform its sensing and stimulation functions. A lead system typically comprises at least one lead, one or more conductor coils, and one or more electrodes. The lead is the insulated wire used to connect the pulse generator of a stimulation device to the cardiac tissue. The lead carries the output stimulus from the pulse generator to the heart and, in demand modes, relays intrinsic cardiac signals back to the sensing circuitry of the stimulation device. Typically, a single-chamber stimulation device requires one lead, whereas a dual-chamber stimulation device requires two leads (one for the atrium and another for the ventricle). The conductor coil is the internal core of the pacing lead through which current flows between the pulse generator and the electrodes.

A lead may be unipolar or bipolar. A unipolar lead is a pacing lead having one electrical pole external to the pulse generator, which is usually located in the heart. The unipolar lead has one conductor coil. The electrical pole is typically a stimulating cathode (i.e., negative pole) at the distal tip of the lead. As used herein, a distal end of the lead is the end which is farther away from the stimulation device. A proximal end of the lead is the end which is connects to the stimulation device. The cathode is the electrode through which a stimulating pulse is delivered. The anode electrode (i.e., the positive pole) is the case, or housing, of the stimulation device. A stimulating pulse returns to the anode using the body tissue as a return current path. A unipolar lead is relatively small in size and is theoretically more reliable than a bipolar lead. However, a unipolar lead/pacing system is more susceptible to interference by other electrical activity in a patient's body, such as inhibition due to myopotentials, and further may be prone to pectoral stimulation.

On the other hand, a bipolar lead is a pacing lead with two electrical poles that are external to the pulse generator. The bipolar lead has two conductor coils. The stimulating cathode is typically at the distal tip of the pacing lead, while the anode is an annular (i.e., ring) electrode which is few millimeters proximal to the cathode. As such, bipolar leads are less prone to pectoral stimulation. A bipolar lead has better signal-to-noise ratio than that of a unipolar lead, and thus, is less susceptible to interference from myopotential inhibition.

In practice, the cathode (i.e., stimulating) electrode is typically placed in contact with the heart tissue in order to stimulate the cardiac tissue. The anode electrode, however, does not need to be in contact with the heart tissue, since blood tends to conduct electrical currents better than the tissue itself. Nonetheless, it is preferable to have the sensing electrode in contact with the heart tissue to allow the detection of more distinct signals. For more details on bipolar lead structure and electrode placement, reference is made to commonly-assigned U.S. Pat. No. 5,522,855, issued to Hoegnelid on Jun. 4, 1996, and is incorporated herein in its entirety by reference. Moreover, for details on quadrapolar (four electrodes) lead structure and electrode placement, reference is made to commonly-assigned U.S. Pat. No. 5,304,219, issued to Chernoff et al. on Apr. 19, 1994, and is incorporated herein in its entirety by reference.

While bipolar leads are reknown for their improved sensing characteristics, some physicians still prefer unipolar leads since the additional stiffness of the bipolar leads makes them handle differently. Programmable polarity has the known advantage of permitting physicians the ability to implant the leads of choice and stock only one stimulation device model that can handle both leads. Further, if bipolar leads are initially implanted, the polarity can be modified based on the patient's needs.

There has been a long felt need to simplify the implantation of dual-chamber stimulation devices by using only one lead, commonly referred to as a "single-pass" lead. The earliest known single-pass leads was a "multi-polar" device (1974) by Berkovits (U.S. Pat. No. 3,825,015) in which two electrodes were placed in the ventricle and four electrodes were placed in the atrium, however, only the best two of the four atrial electrodes were used ultimately.

"Quadrapolar" leads (1975) were attempted by Woollons et al. (U.S. Pat. No. 3,903,897) in which two electrodes were located in the apex of the ventricle and two "floating" electrodes in the atrium. However, these leads were very stiff, and positioning the atrial electrodes to make contact were difficult.

Both of these systems were extremely stiff, and either had poor contact with atrium or had extremely large, complicated connectors.

One of the simplest single-pass leads was a two-electrode lead (1979) by O'Neill (U.S. Pat. No. 4,154,247) in which an electrode was placed in each of the atrium and the ventricle.

Of course, pacing thresholds were also improved upon by forcing the atrial electrode(s) to make direct contact with the cardiac tissue. This may be achieved by either pre-forming the lead in the region of the atrial electrode (as in the '247 patent, supra) or by using various anchoring or active fixation techniques by Grassi (U.S. Pat. No. 4, 624,265) and Hess (U.S. Pat. No. 4,664,120).

Later, "tripolar" electrodes were developed with two electrodes in the apex of the ventricle and a single electrode in the atrium (see U.S. Pat. No. 4,585,004 to Brownlee). Other attempts at tripolar electrodes included a single electrode in the ventricle, with two electrodes in the atrium (see U.S. Pat. Nos. 4,711,027 (Harris); 4,962,767 (Brownlee); and also 5,172,694 (Flammang)).

These tripolar leads of the prior art are chosen since they permit synchonicity between the atrial and ventricular chambers of the heart while providing a less stiff lead, with a smaller proximal connector (which affords a small, less complicated connector on the stimulating device) and without resorting to implanting an additional lead.

For purposes of delivering high voltage shocks, a "defib lead" typically has at least one, and preferably two, transvenously placed shocking coils. While sensing may occur between a ventricular tip electrode and a ventricular ring electrode, it is also known to sense in an "integrated bipolar" fashion between the ventricular tip and a ventricular coil electrode (or between the atrial electrode and an SVC coil electrode).

However, these prior art leads do not offer full programmability of the electrode polarity with a simplified lead structure for ease of manufacture and improved reliability. Accordingly, there is a need in the cardiac pacing technology to offer a lead system which offer programmability, is compactly structured, can be easily placed in a patient's heart and, therefore, is inherently more reliable.

SUMMARY OF THE INVENTION

To overcome the above-mentioned problems, the invention provides an improved single-pass lead comprising three electrodes suitable for sensing intrinsic cardiac activity in two chambers of the heart, for stimulating cardiac tissue in at least the ventricle, and having programmable unipolar or bipolar polarity.

In a first embodiment, suitable for use in an implantable pacemaker having a "VDD" mode, one tip electrode is located at the distal end in the ventricle, one ring electrode is "floating" in the atrium, and a second ring electrode is positioned near or just below the tricuspid valve.

In a second embodiment, suitable for use with an implantable cardioverter-defibrillator device, one tip electrode is located at the distal end in the ventricle, one ring electrode is "floating" in the atrium, and the second electrode is a coil electrode positioned in the ventricle proximal to the tip electrode and extends near or just below the tricuspid valve.

Hereinafter, the second electrode will be referred to as the "tricuspid electrode", regardless of the type or exact construction, and will be construed to cover any electrode in proximity to the tricuspid valve.

Ventricular pacing and sensing can occur in a unipolar fashion from the distal tip electrode to the stimulation device housing (also known as the case electrode), or in a bipolar fashion from the tricuspid electrode to the ventricular tip electrode.

Atrial sensing can be achieved in a unipolar fashion from the atrial ring electrode to the housing, or in a bipolar fashion from the atrial ring electrode to the tricuspid electrode.

While the preferred embodiment is directed toward a lead suitable for VDD pacing and sensing, the present invention could be adapted to include DDD pacing and sensing if the atrial ring electrode/lead body was dimensioned so as to make contact with cardiac tissue, such as near the SA node or the atrial appendage, by preforming the lead in the region of the atrial ring electrode.

Advantageously, sensing of atrial and ventricular cardiac signals is enhanced, since the dipole created between the tricuspid electrode and either the ventricular tip electrode or the atrial ring electrode is larger (i.e., the electrodes are separated by a larger distance than standard bipolar lead arrangements). The present invention thereby detects a larger differential signal than conventional bipolar leads, is immune to myopotential signals, and still is less likely to cause pectoral stimulation.

Furthermore, the single-pass lead of the present invention adds only one additional conductor and electrode to a conventional bipolar lead, and thus is easier to implant, more reliable, and also easier to manufacture.

BRIEF DESCRIPTION OF THE DRAWINGS

The above and other aspects, features and advantages of the invention will be better understood by referring to the following detailed description, which should be read in conjunction with the accompanying drawings, in which:

FIG. 2 is a schematic diagram of the structure of the single-pass lead as implemented in FIG. 1; and FIG. 3 is a schematic diagram of second embodiment of the single-pass lead using a preformed lead, as placed in patient's heart.

DETAILED DESCRIPTION OF THE PREFERRED EMBODIMENT

In one embodiment, the invention provides a lead having three electrodes (tripolar) for use with an implantable stimulation device, such as a pacemaker. The tripolar lead supports bipolar pacing in the ventricle, and bipolar sensing in the atrium and ventricle of a patient's heart. This tripolar lead improves the reliability of the pacemaker operation while reducing the size of the packaging associated with the lead structure. Moreover, an in-line tripolar system reduces the size of the connector block, thereby also reducing the overall size of the implantable pacemaker.

Figure 1:
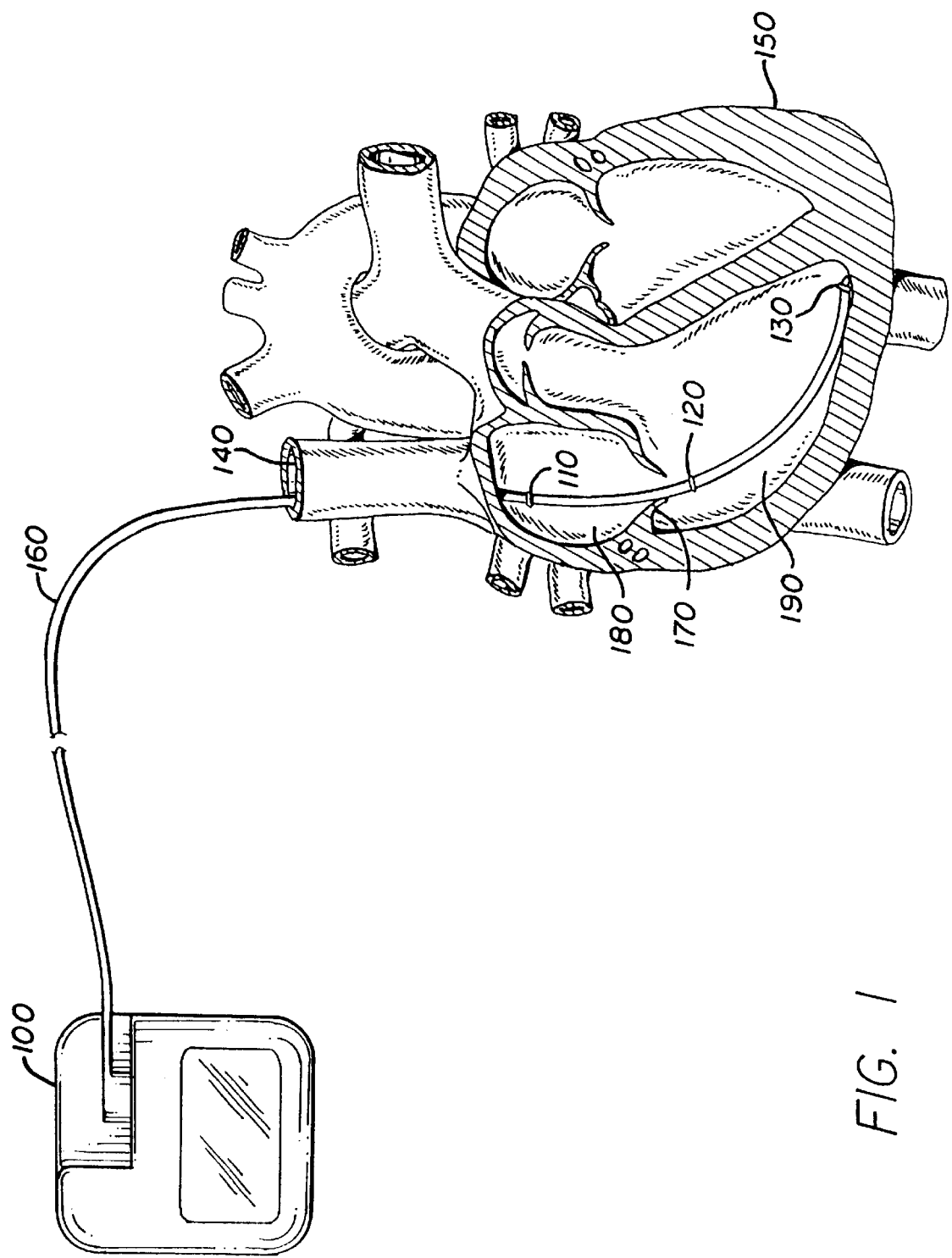
FIG. 1 is a schematic diagram of one embodiment of the single-pass lead suitable for use in a pacemaker as placed in patient's heart.

FIG. 1 is a schematic diagram of one embodiment of the tripolar lead as placed in patient's heart. As shown in FIG. 1, a pacemaker 100 is typically implanted inside a human patient's body to sense and pace the patient's heart 150. The heart 150 includes, among other things, a right atrium 180, a right ventricle 190, a superior vena cava (SVC) 140, and a right atrioventricular (tricuspid) valve 170.

In the preferred embodiment, the lead of the invention be used with a dual-chamber pacemaker, such as a VDD or VDDR pacemaker. A VDD pacemaker is one that paces in the ventricle 190, and senses in both the atrium 180 and ventricle 190. A VDDR pacemaker has characteristics similar to that of the VDD pacemaker with the added capability of rate modulation from input by an independent sensor. Rate modulation refers to the ability of the pacemaker to adjust its pacing rate in response to the patient's physical activity or metabolic demand.

A single lead 160 is typically inserted in the patient's heart 150 through the SVC 140. In the preferred embodiment, the single lead 160 comprises three electrodes: an atrial ring electrode 110, a "tricuspid" ring electrode 120, and a ventricular tip electrode 130.

The atrial ring electrode 110 is preferably positioned inferior to the SVC 140 inside the atrium 180. As noted above, the atrial ring electrode 110 does not have to be placed in contact with the heart tissue for sensing purposes.

The tricuspid electrode 120 is shown in FIG. 1 as a ring electrode positioned just distal to (below) the tricuspid valve 170 inside the ventricle 190.

The ventricular tip electrode 130 is preferably positioned in contact with the heart tissue within the apex region inside the ventricle 190.

The lead connectors (not shown) for these electrodes preferably conform to international standard (IS-1) specifications for two of the electrodes (i.e., similar to conventional bipolar arrangements), but as yet, there is no requirement for tripolar leads.

Using a VDD (or VDDR) pacemaker, the unique lead structure and electrode placement of this invention allows bipolar pacing in the ventricle 190. During bipolar ventricular pacing (i.e., duration of a pacing spike), current flows from the ventricular tip electrode 130 to the heart tissue (i.e., myocardium) to the tricuspid electrode 120 to complete the current flow. Thus, in the present invention, the tricuspid electrode 120 is designated as the anode electrode. With the placement of the tricuspid electrode 120 inside the ventricle 190 (below the tricuspid valve 170), anodal stimulation to the atrium during VDD pacing is avoided.

Moreover, this single-pass lead provides bipolar sensing in the atrium 180 and ventricle 190. Hence, the tricuspid electrode 120 and ventricular tip electrode 130 are used as pacing and sensing electrodes in the ventricle 190. To bipolarly sense in the ventricle 190, ventricular activity is detected by measuring the differential signal (as is well known in the art) between the tricuspid electrode 120 and ventricular tip electrode 130.

The atrial ring electrode 110 and tricuspid ring electrode 120 are used as sensing electrodes in the atrium 180. As such, atrial activity is detected by measuring the differential signal (as is well known in the art) between the atrial ring electrode 110 and tricuspid ring electrode 120.

FIG. 2 is a schematic diagram of the structure of the tripolar lead as applied to the heart in FIG. 1. As shown in FIG. 2, the tripolar lead 160 comprises a first conductor 210, a second conductor 220, and a third conductor 230. These conductors are typically made of low resistance materials, such as Elgiloy, alloys of platinum-iridium, nickel-cobalt, or similar material, which is well known in the art.

In one embodiment, a multifilar conductor may be employed to provide redundancy. The embodiment in FIG. 2 further illustrates a multi-lumen configuration in which each of the conductors are contained within a separate lumen within an insulation material 240. The insulation material 240 may be any electrically resistive material which prevents current flow between the conductors and body tissue. Typical lead insulation materials include silicone rubber, polyurethane, or similar matter which is well known in the art. For thinner leads, a multifilar, coaxial arrangement could be achieved if each of the conductors are mutually isolated by an insulating material, as is known in the art.

The conductors 210, 220, and 230 terminate with the atrial ring electrode 110, tricuspid ring electrode 120, and ventricular tip electrode 130, respectively. These electrodes may be made of activated carbon electrode (ACE) material, titanium nitride on titanium, platinum/iridium alloy, or similar material which is well known in the art. The atrial ring electrode 110 and tricuspid ring electrode 120 are typically annular in shape, whereas the ventricular tip electrode 130 is in a shape of a tip. The distances between the placement of these electrodes may vary from patient to patient. As a general guideline, the distance between the pacemaker and the atrial ring electrode 110 is about 38–50 centimeters (cm), and preferably about 44 cm. The distance separating the atrial ring electrode 110 and the tricuspid ring electrode 120 is about 5–10 cm, and preferably about 8 cm. The distance separating the tricuspid ring electrode 120 and the ventricular tip electrode 130 is about 3–7 cm, and preferably about 5 cm.

In an alternate embodiment, where atrial stimulation is desired, the lead body is pre-formed in the region of atrial ring electrode 110, as shown in FIG. 3, to force the atrial ring electrode to make contact with cardiac tissue and achieve lower stimulation thresholds. Pre-forming leads to get a desired placement is well known in the art. See, for example, U.S. Pat. No. 4,154,247 (O'Neill), which is hereby incorporated by reference herein.

Figure 4:
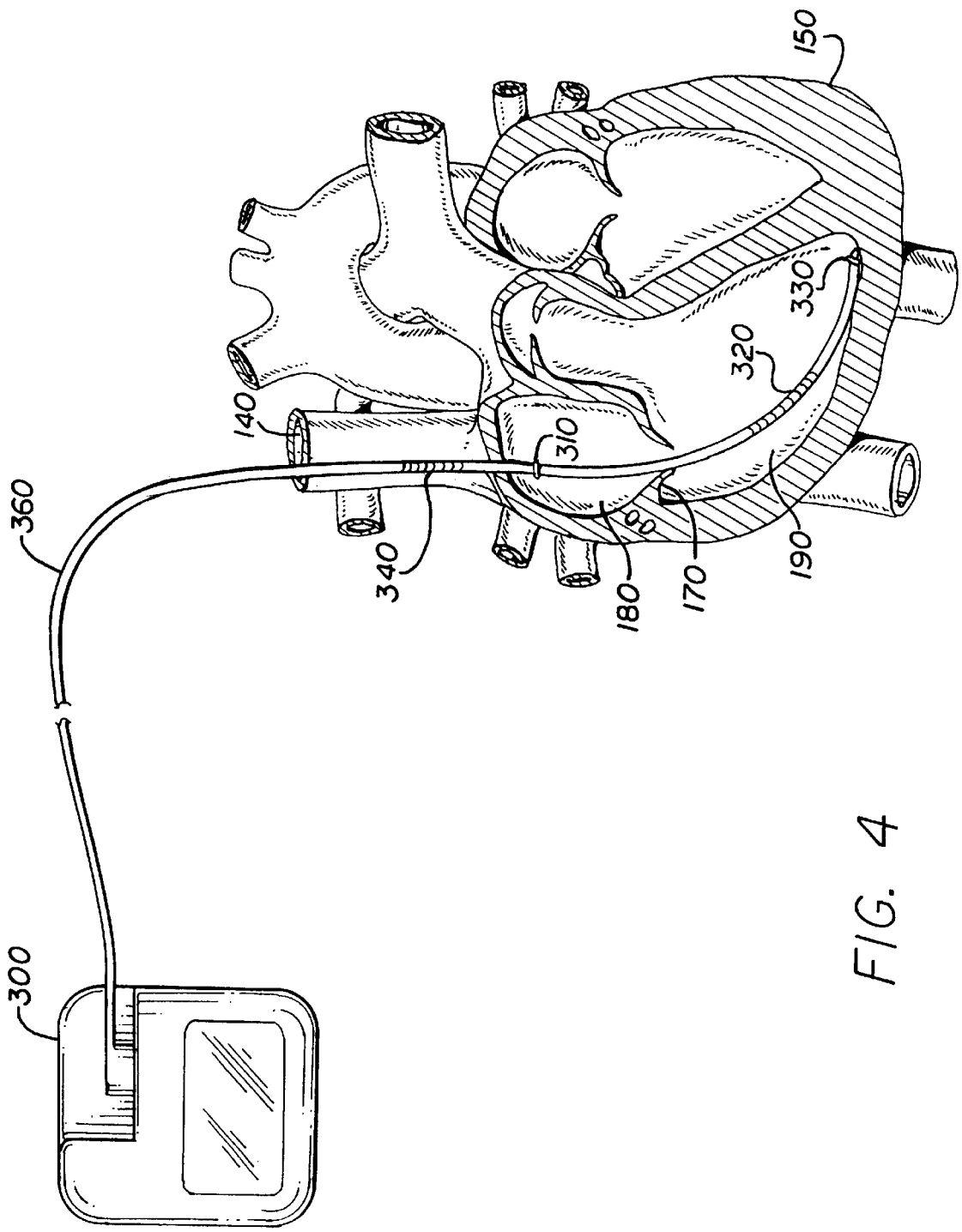
FIG. 4 is a schematic diagram of third embodiment of the single-pass lead suitable for use in an ICD as placed in patient's heart.

FIG. 4 is a schematic diagram of a second embodiment of the single-pass lead as placed in patient's heart for use with an implantable shocking device 300, such as a cardioverter, defibrillator or a combination device with shocking and pacing capabilities.

As shown in FIG. 4, the shocking device 300 is typically implanted inside a human patient's body to sense cardiac signals the patient's heart 150 and to tread pathological arrhythmias.

A single-pass lead 360 is typically inserted in the patient's heart 150 through the SVC 140. In the preferred embodiment, the single lead 360 comprises three electrodes: an atrial ring electrode 310, a coil electrode 320 in the ventricle and in close proximity to the tricuspid value so as to facilitate sensing in the atrium, and a ventricular tip electrode 330.

The atrial ring electrode 310 is preferably positioned similar to the atrial ring electrode 110 (FIG. 1).

The ventricular tip electrode 330 is preferably positioned in contact with the heart tissue within the apex region inside the ventricle 190.

The unique lead structure and electrode placement of this invention allows bipolar pacing in the ventricle 190 using the coil electrode 320 as the reference electrode for both the atrial electrode 310 and the ventricular electrode 330, as described in detail above.

In this embodiment, sensing may occur between (a) a ventricular tip electrode and a ventricular coil electrode, also known as "integrated bipolar" ventricular sensing; (b) between the atrial electrode and the SVC coil electrode, also known as "integrated bipolar" atrial sensing; (c) between the atrial electrode and the ventricular coil electrode, in a "bipolar-fashion" (that is, a "pseudo-integrated bipolar" because the reference electrode is in the ventricle and not the atrium); (d) between the ventricular tip electrode and the housing of the device, in a conventional unipolar fashion; and (e) between the atrial electrode and the housing of the device (also in a conventional unipolar fashion.)

Figure 5:
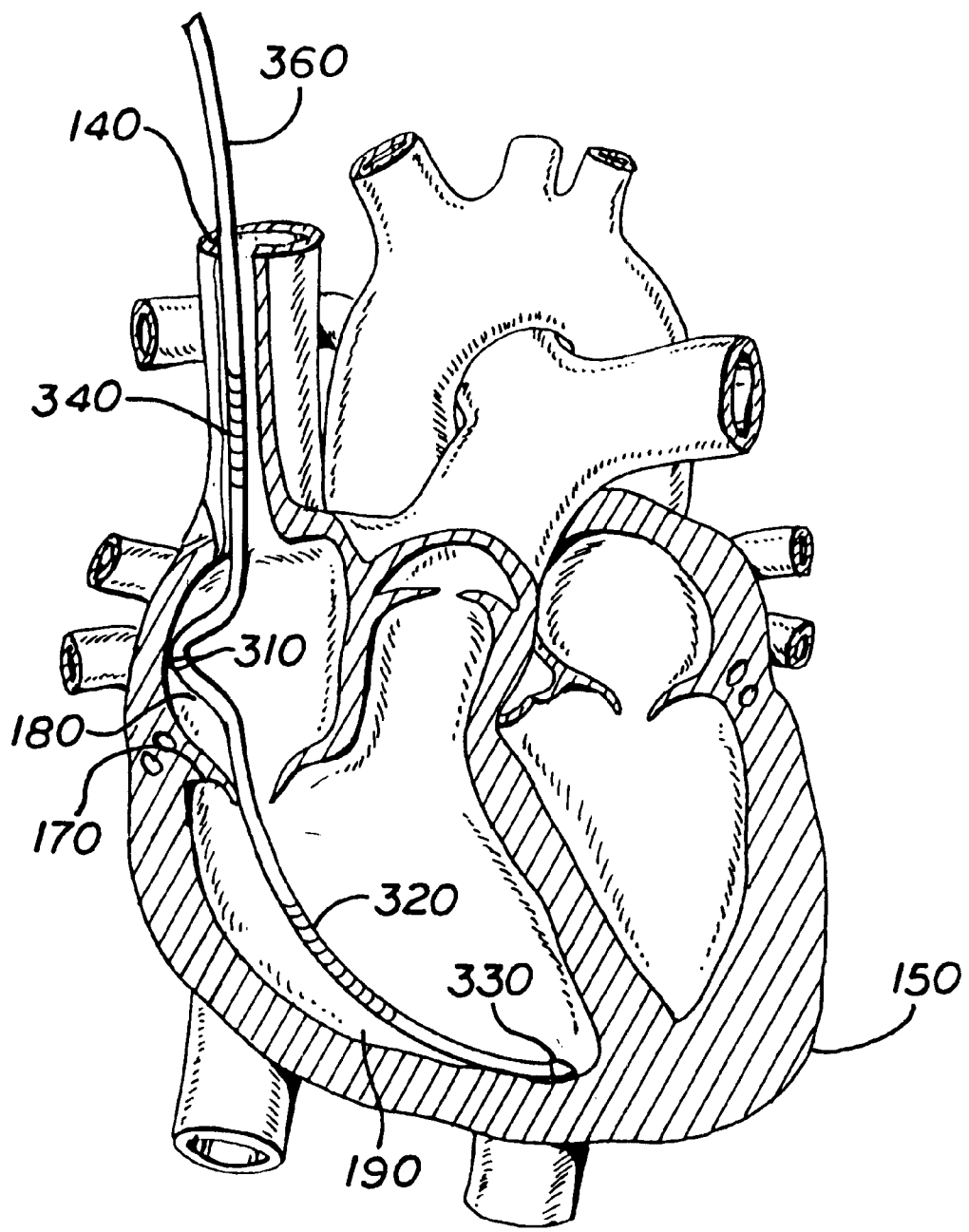
FIG. 5 is a schematic diagram of another embodiment of the single-pass lead for an ICD using a pre-formed lead, as placed in patient's heart.

In an alternate embodiment shown in FIG. 5, where atrial stimulation is desired, the lead body 360 is preformed in the region of atrial ring electrode 310 to force the atrial ring electrode 310 to make contact with cardiac tissue and achieve lower stimulation thresholds.

In view of the foregoing, it will be appreciated that the present invention overcomes the long-standing need for performing VDD pacing in a bipolar fashion, with all of its inherent advantages, using a tripolar electrode. It will further be appreciated that the present invention provides a single-pass shocking lead with a plurality of polarity combinations.

The invention may be embodied in other specific forms without departing from its spirit or essential characteristics. The described embodiment is to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An implantable stimulation system suitable for sensing cardiac signals in a patient's atrium and ventricle and stimulating at least the ventricle, the system comprising:

a single-pass lead that includes a first electrode located on the lead so as to be positioned in the atrium, a second electrode located on the lead and configured as a shocking coil electrode so as to be positioned in the ventricle in close proximity to the tricuspid valve, and a third electrode located on the lead so as to be positioned in the apex of the ventricle, the lead further having a lead body having a connector adapted to make electrical contact to the implantable stimulation device, and at least three conductors adapted to couple the first, second and third electrodes to the connector; and an implantable stimulation device having a sensing circuit that senses atrial signals and a pulse generator that triggers ventricular stimulation pulses based on the sensed atrial signals;

wherein the sensing circuit is capable of sensing atrial signals between the first and second electrodes, and is capable of sensing ventricular signals between the second and third electrodes.

2. The system as defined in claim 1, wherein: the lead body comprising a pre-formed region about the first electrode so as to make electrical contact with the cardiac tissue; and the pulse generator generates stimulation pulses to the first electrode based on the absence of sensed atrial signals.

* * * * *